United States Patent
Abenaim

(10) Patent No.: US 10,281,481 B2
(45) Date of Patent: May 7, 2019

(54) HIGH THROUGHPUT SAMPLE ANALYZER

(75) Inventor: Daniel Abenaim, Lynnfield, MA (US)

(73) Assignee: Analogic Corporation, Peabody, MA (US)

(*) Notice: Subject to any disclaimer, the term of this patent is extended or adjusted under 35 U.S.C. 154(b) by 925 days.

(21) Appl. No.: 13/642,162

(22) PCT Filed: Apr. 20, 2010

(86) PCT No.: PCT/US2010/031692
§ 371 (c)(1),
(2), (4) Date: Oct. 19, 2012

(87) PCT Pub. No.: WO2011/133141
PCT Pub. Date: Oct. 27, 2011

(65) Prior Publication Data
US 2013/0035242 A1    Feb. 7, 2013

(51) Int. Cl.
C40B 60/10 (2006.01)
C40B 20/00 (2006.01)
G01N 35/02 (2006.01)

(52) U.S. Cl.
CPC .................... *G01N 35/02* (2013.01)

(58) Field of Classification Search
None
See application file for complete search history.

(56) References Cited

U.S. PATENT DOCUMENTS

| 2006/0153745 A1* | 7/2006 | Ermakov | B01J 19/0046 422/130 |
| 2006/0201810 A1* | 9/2006 | Paschetto | B01L 3/0244 204/470 |
| 2006/0210435 A1* | 9/2006 | Alavie et al. | 422/65 |
| 2007/0140925 A1* | 6/2007 | Phelps | B01J 19/0046 422/130 |
| 2008/0038827 A1 | 2/2008 | Miller et al. | |
| 2008/0227663 A1* | 9/2008 | Tisone | B01J 19/0046 506/39 |

(Continued)

FOREIGN PATENT DOCUMENTS

| EP | 1248113 A1 | 10/2002 | |
| WO | 02/49761 A2 | 6/2002 | |
| WO | WO 2008055915 A2 * | 5/2008 | B01J 19/0046 |

OTHER PUBLICATIONS

International search report for PCT/US2010/031692 published as WO 2011/133141 A1.

(Continued)

*Primary Examiner* — Benjamin R Whatley
(74) *Attorney, Agent, or Firm* — TraskBritt

(57) ABSTRACT

A sample processing system includes a sample carrier support configured to concurrently support multiple sample carriers in series, each sample carries carrying a respective sample to be processed. The apparatus also includes a plurality of processing stations located at different positions along the sample carry support, each processing station configured to perform a different processing act of a plurality of processing acts to be performed on each sample. The apparatus further includes a support mover that moves the sample support and hence the sample carriers sequentially from processing station to processing station for processing.

17 Claims, 4 Drawing Sheets

(56) References Cited

U.S. PATENT DOCUMENTS

| | | | |
|---|---|---|---|
| 2009/0253181 A1* | 10/2009 | Vangbo | G01N 27/44791 435/91.1 |
| 2010/0009871 A1* | 1/2010 | Reed | B01J 19/0046 506/26 |
| 2010/0075430 A1* | 3/2010 | Hofstadler | G01N 35/0098 436/94 |
| 2011/0014606 A1* | 1/2011 | Steinmetzer | B01J 19/0046 435/6.11 |
| 2011/0256031 A1* | 10/2011 | Parker | B01J 19/0046 422/131 |
| 2012/0082985 A1* | 4/2012 | Zenhausern | B01L 3/5027 435/6.12 |

OTHER PUBLICATIONS

Wikipedia, Biochip, Wikipedia, the free encyclopedia, page last modified on Mar. 30, 2010, 6 sheets, http://en.wikipedia.org/wiki/Biochip.

Wikipedia, DNA Sequencer, Wikipedia, the free encyclopedia, page last modified on Dec. 16, 2009, 2 sheets, http://en.wikipedia.org/wiki/DNA_sequencer.

Wikipedia, DNA Sequencing, Wikipedia, the free encyclopedia, page last modified on Mar. 30, 2010, 10 sheeets, http://en/wikipedia.org/wiki/DNA_sequencing.

Wikipedia, Lab-on-a-chip, Wikipedia, the free encyclopedia, page last modified on Apr. 8, 2010, 5 sheets, http://en.wikipedia.org/wiki/Lab-on-a-chip.

Wikipedia, DNA microarray, Wikipedia, the free encyclopedia, page last modified on Apr. 8, 2010, 11 sheet, http://en.wikipedia.org/wiki/DNA_microarray.

International Written Opinion received for PCT Patent Application No. PCT/US10/31692, dated Apr. 7, 2011, 10 pages.

International Preliminary Report on Patentability received for PCT Patent Application No. PCT/US10/031692, dated Nov. 1, 2012, 8 pages.

* cited by examiner

HIGH THROUGHPUT SAMPLE ANALYZER

CROSS-REFERENCE TO RELATED APPLICATION

This application is a national phase entry under 35 U.S.C. § 371 of International Patent Application PCT/US2010/031692, filed Apr. 20, 2010, designating the United States of America and published in English as International Patent Publication WO 2011/133141 A1 on Oct. 27, 2011.

TECHNICAL FIELD

This disclosure generally relates to a sample analyzer and is described herein with particular application to a DNA sequencer; however, other sample analysis applications are also contemplated herein.

BACKGROUND

A DNA sequencer is a device that determines an order of the nucleotide bases (adenine, guanine, cytosine, and thymine) in a DNA strand. One DNA sequencer sequences DNA strands carried on a biochip, a lab-on-a-chip, or the like that has a plurality of sample processing regions and micro-channels that go to, from and/or between the sample processing regions. The biochip also includes an interface to a manifold of the sequencer for receiving fluids such as reagents, wash solutions, primers, dyes, etc., and for interfacing with a fluid and sample moving sub-system such as a high-pressure sub-system.

Generally, the DNA strand is moved or advanced under high pressure from a sample processing region to a sample processing region and is processed at each of the sample processing regions. By way of example, with one DNA sequencer, a sample such as a bucchal swab, including a DNA strand, is first processed at an extraction region of the biochip with an extraction sub-system that extracts one or more DNA strands from the sample. An extraction fluid such as a lyses reagent is routed to the region via the micro-channels. The DNA strand is then moved to a purification region of the biochip where a purification sub-system purifies the extracted DNA strand. A purification fluid such as a wash solution is routed to the region via the micro-channels.

The DNA strand is then moved to a replication (thermo-cycling amplification) region of the biochip where the DNA strand is replicated and labeled, e.g., via polymerase chain reaction (PCR) or otherwise by a replication sub-system. Replication and labeling fluids such as a primer and fluorescent dyes are routed to the region via the micro-channels. The DNA strand is then moved to a separation and analysis region of the biochip where a separation sub-system separates the nucleotides, e.g., via capillary electrophoresis or otherwise, and an analysis sub-system sequences the nucleotides, e.g., via an optical detection system. Sequencing has been determined based on dye wavelength, and a signal indicative of the sequence is read out.

One automated DNA sequencer has integrated the above-noted processing sub-systems into a single device. With this sequencer, the biochip is placed in a single test position, and each of the sub-systems sequentially processes the biochip at the test position. The biochip includes the necessary infrastructure (micro-channels, processing regions, etc.) to concurrently interface all of the processing sub-systems and a manifold of the sequencer, which provides the various fluids for the processing and high pressure for moving the DNA strand through the biochip from processing region to processing region. Unfortunately, such a DNA sequencer requires a relatively large number and complex arrangement of micro-channels, valves, interfaces, etc., at the manifold.

With this sequencer, a single biochip is loaded and processed at any given time. A human or machine loads the biochip for processing and unloads the biochip after processing. As a consequence of the foregoing, biochip-to-biochip processing can be a relatively lengthy and slow process. A trend has been to utilize a DNA sequencer configured to individually process, in parallel, multiple samples carried on a single biochip. Although this technique may increase the number of samples processed during a given time frame, biochip-to-biochip processing still remains a relatively lengthy and slow process. For example, in both instances, the processing time for the first biochip is equal to the aggregate of the processing time of each processing sub-system, and the processing time for each successive biochip, relative to the processing time for a preceding biochip, is also equal to the aggregate of the processing time of each processing sub-system.

BRIEF SUMMARY

Aspects of the application address the above matters, and others.

In one aspect, a sample processing system includes a sample carrier support configured to concurrently support multiple sample carriers in series, each sample carrier carrying a respective sample to be processed. The apparatus also includes a plurality of processing stations located at different positions along the sample carry support, each processing station configured to perform a different processing act of a plurality of processing acts to be performed on each sample. The apparatus further includes a support mover that moves the sample support and hence the sample carriers sequentially from processing station to processing station for processing.

In another aspect, a method includes concurrently processing a plurality of samples respectively on different sample carriers, wherein each sample is serially processed by a plurality of different processing stations located at different positions, and each sample carrier is located at a different processing position respectively corresponding to one of the plurality of different processing stations.

In another aspect, a sample carrier includes a sample carrying region configured to carry a sample for processing by a plurality of different processing acts performed at a plurality of different processing locations by of a plurality of different processing stations, and a processing station interface, including: a plurality of sub-interfaces, each interface respectively corresponding to one of the plurality of different processing stations.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
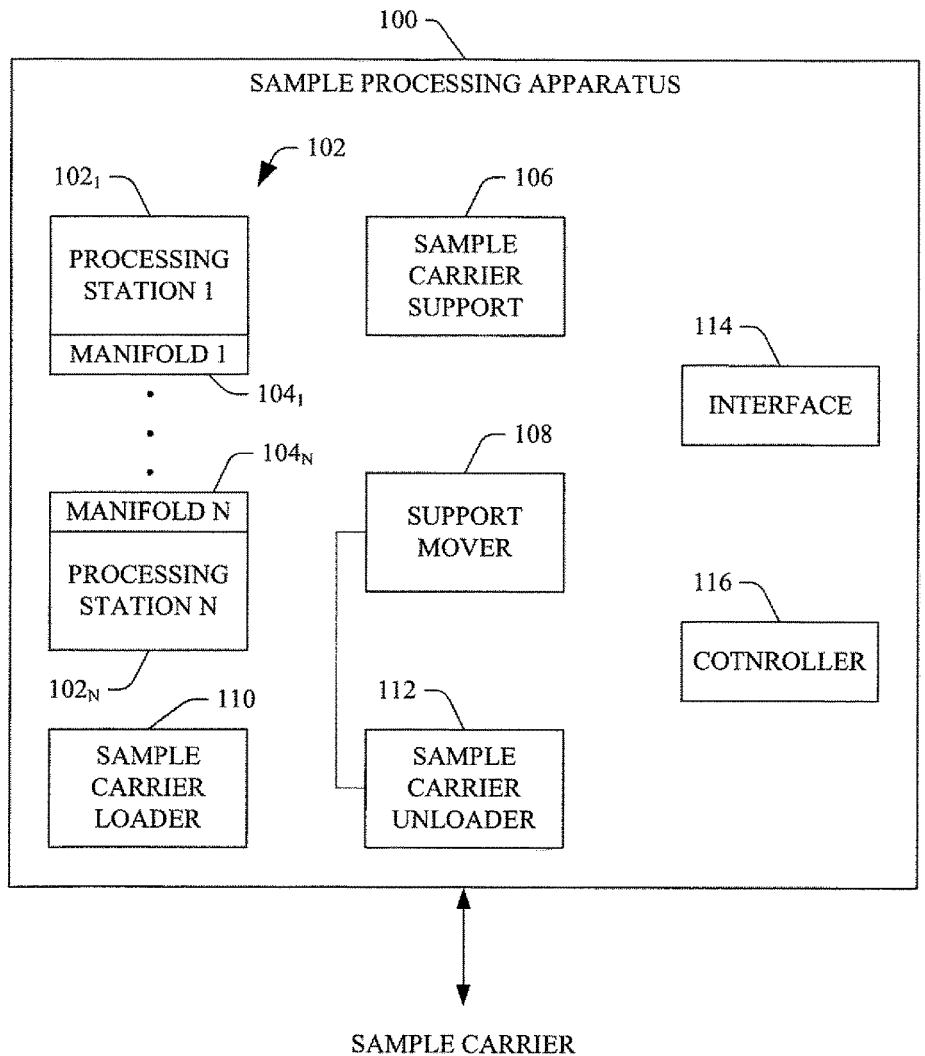
FIG. 1 illustrates an example of a sample processing system, including at least a sample carrier support and a plurality of processing stations.

FIG. 1 illustrates an example of a sample processing apparatus 100.

The apparatus 100 is configured to process one or more samples respectively carried by one or more sample carriers. Non-limiting examples of suitable sample carriers include a biochip, a lab-on-a-chip, and/or other sample carrier. In one instance, the sample carrier also includes microfluidic channels and/or valves for moving the sample from one processing area to the next within the sample carrier. An example of suitable processing includes, but is not limited to, processing bio-samples such as samples containing DNA such as saliva, blood, skin, and/or other bio-samples. Such processing may include, but is not limited to, determining a presence or absence of, identifying, and/or sequencing nucleotide bases (adenine (A), guanine (G), cytosine (C), and thymine (T)) of the DNA in the sample. Additional and/or alternative samples and/or types of processing are also contemplated herein.

The apparatus 100 includes N processing stations $102_1, \ldots, 102_N$ (where N is an integer equal to or greater than one), collectively referred to herein as processing stations 102. The apparatus 100 can be configured to include as many processing stations 102 as there are individual processing acts of the processing of interest that can be performed independently from one another and concurrently in parallel with each other. In the illustrated embodiment, each of the processing stations 102 is configured to carry out a different sub-processing act for a sample carried by a sample carrier loaded therein.

By way of non-limiting example, and continuing with the DNA example, one of the processing stations 102 may be configured to extract one or more DNA strands from a bio-sample. Another processing station 102 may be configured to purify the extracted DNA strand. Another processing station 102 may be configured to replicate (amplify) and label the replicated DNA strand. Another processing station 102 may be configured to separate the nucleotide bases in the DNA strand based on the label. Another processing station 102 may be configured for sequencing the nucleotide bases. It is to be appreciated that the foregoing list is provided for explanatory purposes and is not limiting. In other embodiments, one or more processing stations 102 may be configured for additional and/or alternative processing.

The processing stations $102_1, \ldots, 102_N$ respectively include manifolds $104_1, \ldots, 104_N$, collectively referred to herein as manifolds 104. The manifolds 104 respectively include interfaces for interfacing sample carriers. As described in greater detail below, in one instance, each of the manifolds 104 may be configured to include only the interfaces to perform the processing of the corresponding processing station 102. As such, a particular one of the manifolds 104 may include less channels, valves, etc., relative to a configuration in which the manifold 104 includes channels, valves, etc., for the sub-processing acts performed by two or more, including all, of the different processing stations 102. This may reduce the complexity and/or cost of the manifolds 104.

A sample carrier support 106 is configured to support one or more sample carriers in the sample processing apparatus 100. As described in greater detail below, in one instance, the sample carrier support 106 moves at least one sample carrier from processing station $102_1$ to processing station $102_N$. Where the support 106 is concurrently supporting multiple sample carriers, each sample carrier being located at a different one of the processing stations 102, the sample carrier support 106 concurrently moves the multiple sample carriers from processing station $102_1$ to processing station $102_N$. A support mover 108 is configured to move the sample carrier support 106 and hence the sample carriers from processing station $102_1$ to processing station $102_N$.

A sample carrier loader 110 loads sample carriers into the sample processing apparatus 100, and a sample carrier unloader 112 unloads sample carriers from the sample processing apparatus 100 after the samples are processed. The illustrated loader 110 is configured to serially or sequentially load sample carriers onto the support 106, including loading sample carriers so that a sample carrier is located at each of processing stations 102 during processing. Of course, for the first N−1 sample carriers and the last N−1 sample carriers, there will not be a sample carrier available for each of the processing stations 102. In other embodiments, sample carriers are otherwise loaded. For example, in one instance, only a single sample carrier is loaded for processing. In another example, samples carriers are loaded so that there is a sample carrier at every other processing station 102. Other loading patterns are also contemplated herein.

An interface 114 allows an operator (e.g., human and/or machine) to interact with the sample processing apparatus 100. Such interaction may include providing input (e.g., control, data, etc.) to the sample processing apparatus 100 and/or conveyance and/or presentation of information from the sample processing apparatus 100. A controller 116 controls the various components of the sample processing apparatus 100 including, but not limited to, one or more of the processing stations 102, the manifolds 104, the sample carrier support 106, the support mover 108, the sample carrier loader 110, the sample carrier unloader 112, the interface 114, and/or one or more other components of the sample processing apparatus 100.

By utilizing the different processing stations 102, in parallel, for concurrently processing samples on multiple different sample carriers, different processing acts can be performed concurrently on samples of the different sample carriers. In one instance, this allows for decreasing the time between processing successive sample carriers and hence samples, relative to a configuration in which only one sample carrier is processed at a time. By way of example, the processing time for the first sample carrier loaded corresponds to (e.g., will be equal or about equal to) an aggregate of the time the sample carrier moves through each processing station 102. However, with a sample carrier at each of the processing stations 102, the throughput thereafter for a sample carrier corresponds to (e.g., will be equal or about equal to) the time to complete the longest of the sub-processing acts being performed.

Figure 2:
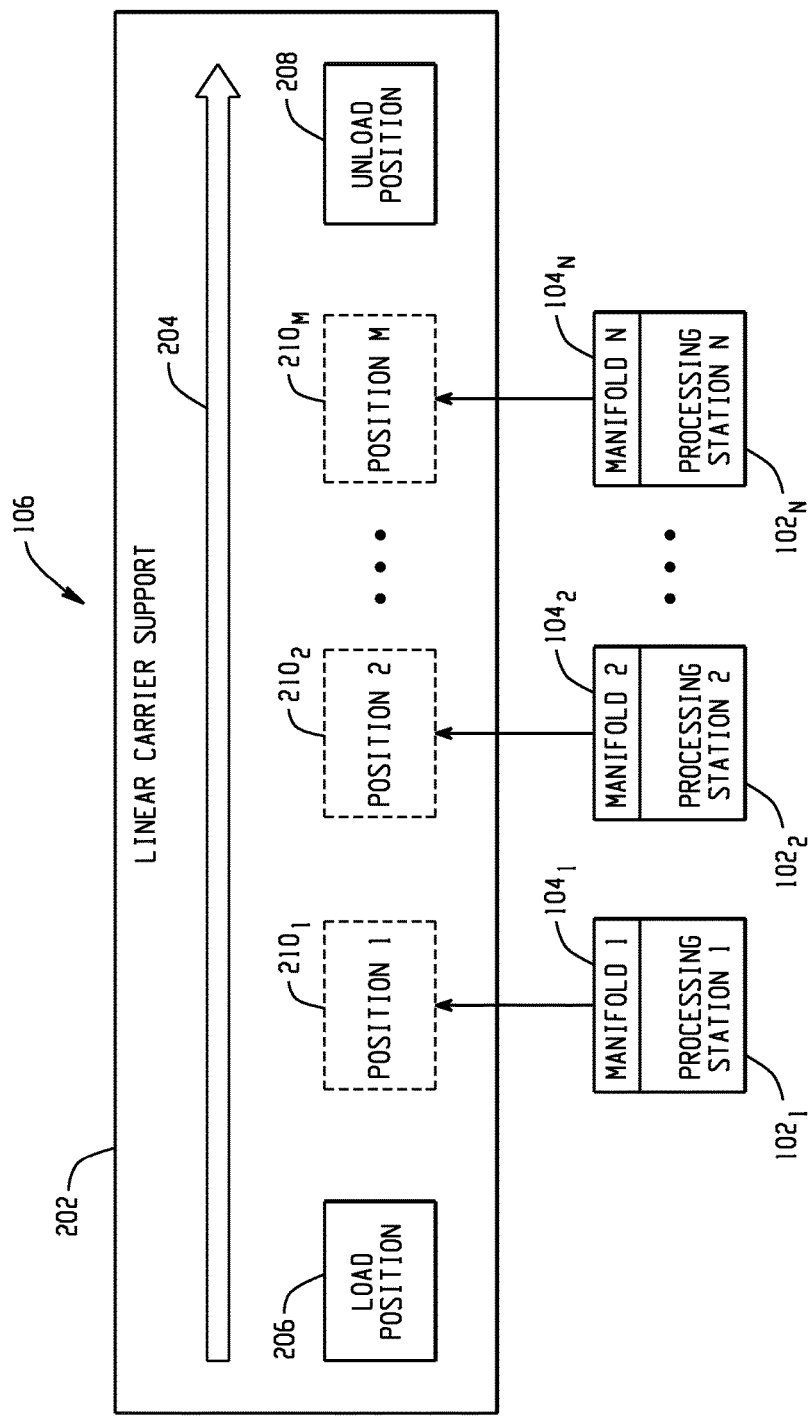
FIG. 2 illustrates an example of a linear sample carrier support.

FIG. 2 illustrates a non-limiting embodiment of an example sample carrier support 106 in connection with the processing stations 102 and manifolds 104. The illustrated sample carrier support 106 includes a linear carrier support 202 that linearly moves sample carriers along a generally linear path 204 from a load position 206 of the support 202 to an unload position 208 of the support 202.

In the illustrated embodiment, the linear carrier support 202 moves a sample carrier loaded at the load position 206 through a plurality of different pre-determined processing positions $210_1, 210_2, \ldots, 210_M$ (where M is an integer equal to or greater than one) to the unload position 208. The processing positions $210_1, 210_2, \ldots, 210_M$ (collectively referred to herein as positions 210) respectively correspond to the different processing stations 102. By way of example, the linear carrier support 202 moves a sample carrier (of a plurality of loaded sample carriers) to the position $210_2$ where the sample carried thereby is processed with the processing station $102_2$. The linear carrier support 202 then moves the sample carrier to a next position where the sample is processed with the next processing station. It is to be appreciated that M may or may not be equal to N.

Figure 6:
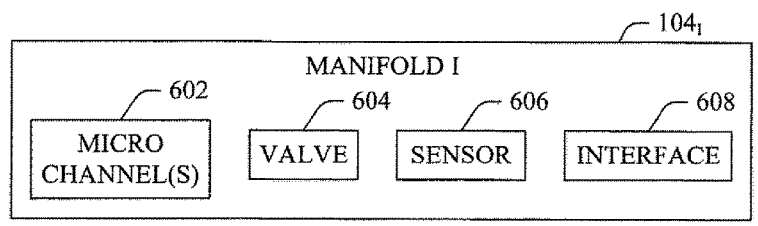
FIG. 6 illustrates an example of a manifold.

As briefly discussed above, each of the manifolds 104 respectively includes interfaces for interfacing with a sample carrier. In the illustrated embodiment, each of the manifolds 104 only includes the micro channels, valves, sensors, pressure control system, and/or other components used for processing samples by the corresponding processing station 102. For example, the manifold $104_1$ may only include interfaces for interfacing with a sample carrier located in the position $210_1$ for processing by the processing station $102_1$. With continuing reference to the DNA example, where the processing station $102_1$ extracts DNA strands from samples, the manifold $104_1$ in this example would only include, for instance, interfaces for supplying extraction reagents and optionally moving the DNA to and/or from the position $210_1$. In another instance, one or more other manifolds 104 may include a different arrangement of components. FIG. 6 shows an example in which a manifold I includes micro channels 602, a valve 604, a sensor 606, and an interface 608.

Figure 3:
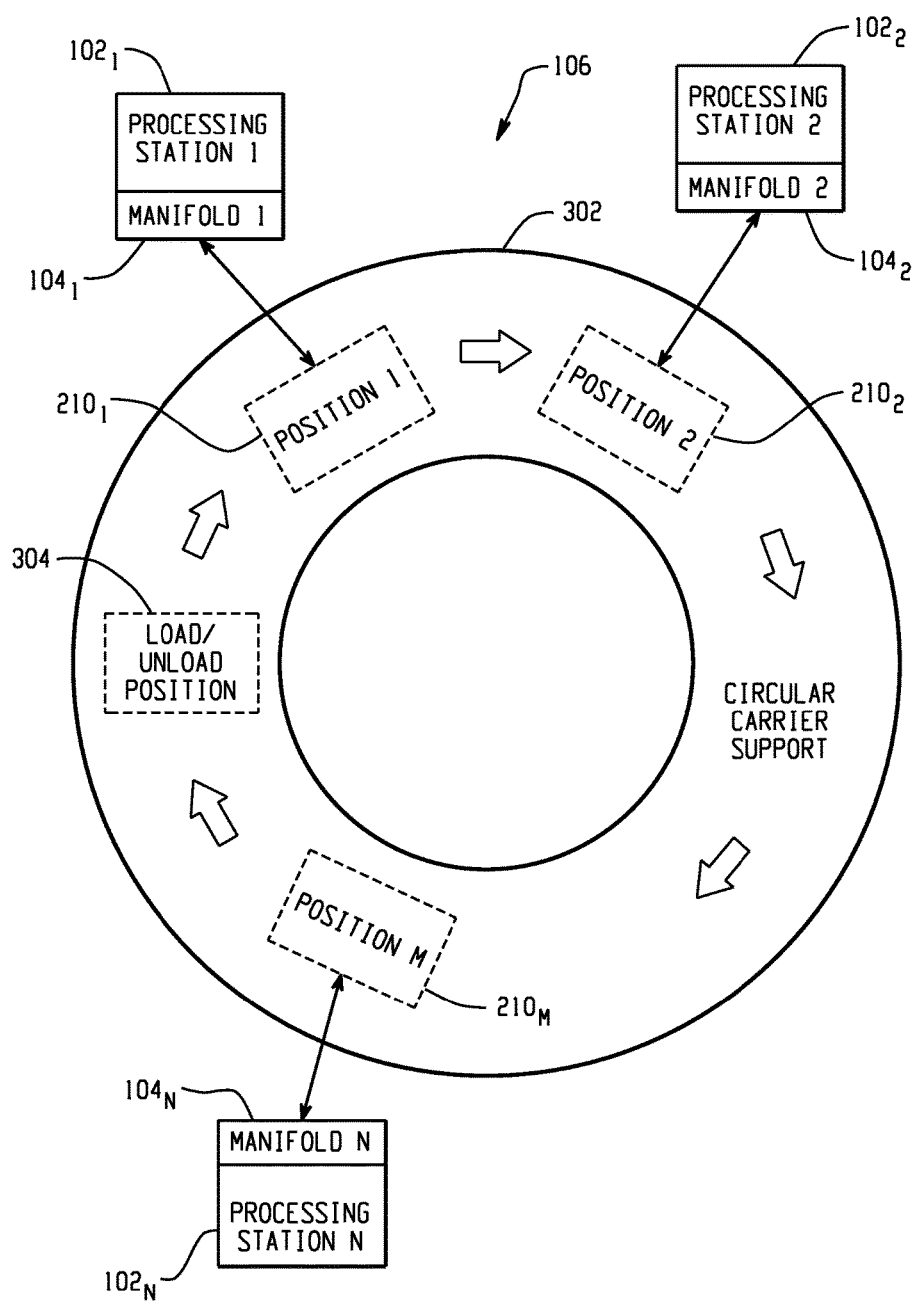
FIG. 3 illustrates an example of a circular sample carrier support.

FIG. 3 illustrates a non-limiting embodiment of an example sample carrier support 106 in connection with the processing stations 102 and manifolds 104. The illustrated sample carrier support 106 includes a circular carrier support 302 that moves sample carriers along a generally circular path from a load/unload position 304 of the support 302 through the plurality of positions 210 back to the load/unload position 304. This configuration, in one instance, can be thought of as a turntable configuration.

In the illustrated embodiment, the load and unload positions are the same position 304. In one instance, when a processed sample carrier is located at the load/unload position 304, the processed sample carrier is unloaded and then a next sample carrier, when another one is available for processing, is loaded to the load/unload position 304. In another embodiment, the load and unload positions are different positions on the support 302, e.g., adjacent or otherwise. In this instance, sample carriers can be separately or concurrently loaded and unloaded.

Figure 4:
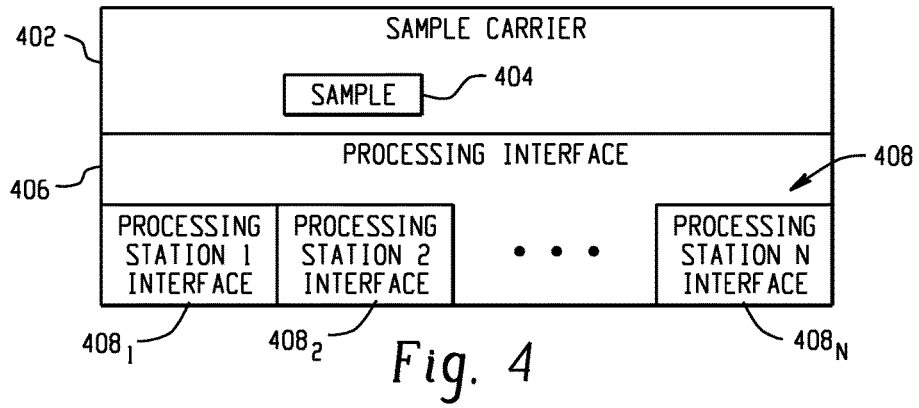
FIG. 4 illustrates an example of a sample carrier.

FIG. 4 illustrates an example sample carrier 402 carrying a sample 404. The sample carrier 402 includes a processing interface 406 that interfaces with the manifolds 104 (FIGS. 1, 2 and 3). As discussed herein, in one instance, a manifold(s) 104 of a processing station(s) 102 may only include the interface components used for processing by the corresponding processing station(s) 102.

The illustrated processing interface 406 is configured with N processing station interfaces $408_1, 408_2, \ldots, 408_N$, collectively referred to herein as processing station interfaces 408. Each of the processing station interfaces 408 is configured to interface with a corresponding one of the manifolds 104. The location of the processing station interfaces 408, in connection with the sample carrier, coincides with the location of the sample of the sample carrier during processing.

Generally, as the sample 404 is processed and moved through the sample carrier 402, the point of connection between the sample carrier 402 (and thus the processing station interface 408) and the manifold 104 for a next processing station 102 shifts. The illustrated embodiment shows separate and distinct connection points for each of the processing station interfaces 408.

In another embodiment, one or more of the processing station interface(s) 408 may partially or fully overlap. This allows for sharing sample carrier channels by multiple processing stations. As such, the total number of channels in a sample carrier 402 may be reduced relative to a configuration in which a sample carrier 402 is not processed via a plurality of processing stations as described herein. By way of example, where K channels are evenly distributed for L processing stations, a sample carrier 402 may only include K/L channels, which are shared by the L processing stations.

Figure 5:
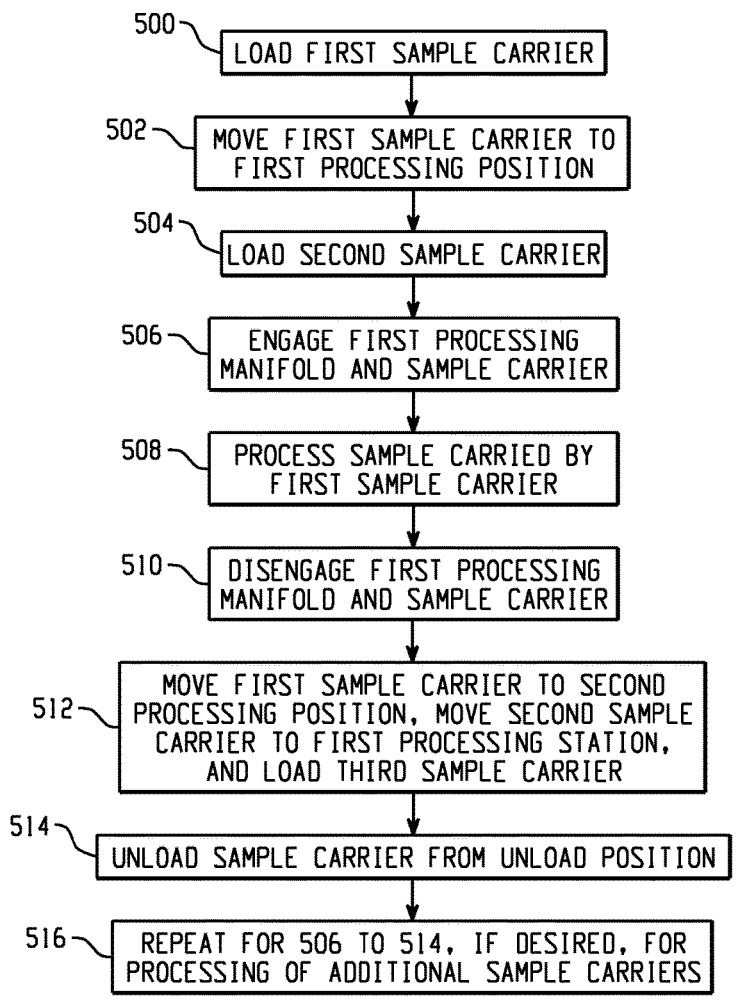
FIG. 5 illustrates an example of a method.

FIG. 5 illustrates a method. It is to be understood that the ordering of the following acts is for explanatory purposes and not limiting. As such, different ordering, including concurrently performed acts, is contemplated herein. In addition, one or more of the following acts may be omitted and/or one or more acts may be included.

At 500, a first sample carrier is loaded at a load position on the sample carrier support 106 of the sample processing apparatus 100. As shown in FIGS. 2 and 3, the sample carrier support 106 may be a generally linear support 202 or a generally circular support 302. In other embodiments, the sample carrier support 106 may include an otherwise shaped support.

At 502, the first sample carrier is moved to the first processing position. In one instance, the load and first processing positions are different positions. In another instance, the load and first processing positions are the same position.

At 504, a second sample carrier is loaded at the load position.

At 506, the manifold for the first processing station engages or otherwise interfaces the first sample carrier.

At 508, the sample carried by the first sample carrier is processed by the first processing station.

At 510, the manifold disengages the first sample carrier.

At 512, the first sample carrier is moved to a subsequent processing position (if any) for subsequent processing, the second sample carrier is moved to the first processing position, and a third sample carrier is loaded at the load position.

At 514, where the subsequent position is the unload position, the sample carrier at the subsequent position is unloaded.

At 516, acts 506-514 are repeated until all sample carriers are processed, processing is terminated or paused, and/or other criteria is satisfied. Note that for each iteration, the loaded sample carriers are advanced to the next processing positions, and that where there is a sample carrier at a processing position, the manifold for that processing position engages and disengages the sample carrier, and the corresponding processing station processes the sample carried by the sample carrier. Also note that where there is no more sample carriers to load, a sample carrier is not loaded.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A DNA sample processing apparatus, comprising:
a sample carrier support with multiple positions in series, including at least a first position and a second position downstream from the first position, configured to concurrently support multiple sample carriers;
a plurality of processing stations in series, including at least a first processing station located at the first position and configured to perform a first processing act in the first position on a sample carried by a sample carrier of the multiple sample carriers located at the first position, and a second processing station located at the second position and configured to perform a second processing act in the second position on a sample carried by a sample carrier of the multiple sample carriers located at the second position,
wherein the first processing station includes a first manifold with a first interface in a first configuration configured to interface with only a first one of a plurality of interfaces of the sample carrier located at the first position and perform only the first processing act, and the second processing station includes a second manifold with a second interface in a second configuration configured to interface with only a second one of the plurality of interfaces of the sample carrier located at the second position and perform only the second processing act, the first and second processing stations are configured to perform the first and second processing acts independently from one another and concurrently in parallel with each other, and the first processing act is selected from a group consisting of a DNA extraction processing act, a DNA purification processing act, a DNA replication and labelling processing act, a DNA nucleotide base separation processing act, and a DNA strand sequencing processing act, and the second processing act is selected from a group consisting of a DNA extraction processing act, a DNA purification processing act, a DNA replication and labelling processing act, a DNA nucleotide base separation processing act, and a DNA strand sequencing processing act, wherein the first processing act and the second processing act are different; and
a support mover configured to move the sample carrier support, and move the sample carrier located at the second position directly to a third position of the multiple positions while moving the sample carrier located at the first position directly to the second position.

2. The sample processing apparatus of claim 1, wherein the sample carrier support is configured to move the sample carrier located at the first position along a linear path to the second position.

3. The sample processing apparatus of claim 1, wherein the sample carrier support is configured to move the sample carrier located at the first position along a circular path to the second position.

4. The sample processing apparatus of claim 1, wherein the first manifold includes a first number of micro-channels and the second manifold includes a second number of micro-channels, and the first number of micro-channels is different than the second number of micro-channels.

5. The sample processing apparatus of claim 1, wherein the first manifold includes a first number of valves and the second manifold includes a second number of valves, and the first number of valves is different than the second number of valves.

6. The sample processing apparatus of claim 1, wherein the first manifold interface is configured to interface only with the sample carrier located at the first position.

7. The sample processing apparatus of claim 1, wherein the multiple positions further comprise a load position, wherein the sample carrier support is configured to receive the multiple sample carriers at the load position.

8. The sample processing apparatus of claim 7, wherein none of the plurality of processing stations are located at the load position.

9. The sample processing apparatus of claim 1, wherein the multiple positions further comprise an unload position, wherein the sample carrier support is configured to offload the multiple sample carriers at the unload position.

10. The sample processing apparatus of claim 7, wherein none of the plurality of processing stations are located at the unload position.

11. The sample processing apparatus of claim 1, wherein the multiple positions further comprise an unload position and a load position, wherein the sample carrier support is configured to receive the multiple sample carriers at the load position and to offload the multiple sample carriers at the unload position.

12. The sample processing apparatus of claim 1, wherein the multiple positions further comprise a loading position, wherein the sample carrier support is configured to receive and offload the multiple sample carriers at the loading position.

13. The sample processing apparatus of claim 1, wherein the multiple positions further comprise at least a fourth position and a fifth position, the plurality of processing stations further comprise a third processing station, a fourth processing station, and a fifth processing station, and the third processing station is located at the third at position and configured to perform a third processing act on a sample carried by a sample carrier of the multiple sample carriers located at the third position, the fourth processing station is located the fourth position and configured to perform a fourth processing act on a sample carried by a sample carrier of the multiple sample carriers located at the fourth position, and the fifth processing station is located at the fifth at position and configured to perform a fifth processing act on a sample carried by a sample carrier of the multiple sample carriers located at the fifth position.

14. The sample processing apparatus of claim 13, wherein the first processing act is the DNA extraction processing act, the second processing act is the DNA purification processing act, the third processing act is the DNA replication and labelling processing act, the fourth processing act is the DNA nucleotide base separation processing act, and the fifth processing act is the DNA strand sequencing processing act.

15. The sample processing apparatus of claim 13, wherein the carrier support is configured to directly carry each of the multiple sample carriers directly from the first position to the second position, directly from the second position to the third position, directly from the third position to the fourth position, and directly from the fourth position to the fifth position.

16. The sample processing apparatus of claim 15, wherein multiple positions further comprise a load position and an unload position, wherein the load position is located before the first position and the unload position is located after the fifth position, and wherein the carrier support is configured to carry each of the multiple sample carriers directly from the load position to the first position and directly from the fifth position to the unload position.

17. The sample processing apparatus of claim 1, wherein the first processing station is configured to perform only the DNA extraction processing act, and the interface of the first manifold is configured only to supply a DNA extraction agent.

\* \* \* \* \*

UNITED STATES PATENT AND TRADEMARK OFFICE
CERTIFICATE OF CORRECTION

PATENT NO. : 10,281,481 B2
APPLICATION NO. : 13/642162
DATED : May 7, 2019
INVENTOR(S) : Daniel Abenaim It is certified that error appears in the above-identified patent and that said Letters Patent is hereby corrected as shown below:

On the Title Page
In ITEM (57) ABSTRACT, Line 3, change "sample carries carrying" to --sample carrier carrying--

In the Claims
Claim 13, Column 8, Line 39, change "located the fourth" to --located at the fourth--

Signed and Sealed this
Ninth Day of July, 2019

Andrei Iancu
*Director of the United States Patent and Trademark Office*